United States Patent
Diamond (10) Patent No.: US 8,527,035 B2
(45) Date of Patent: Sep. 3, 2013

(54) SYSTEM, OPTODE AND CAP FOR NEAR-INFRARED DIFFUSE-OPTICAL FUNCTION NEUROIMAGING

(75) Inventor: Solomon G. Diamond, Quincy, MA (US)

(73) Assignee: The Trustees of Dartmouth College, Hanover, NH (US)

( * ) Notice: Subject to any disclaimer, the term of this patent is extended or adjusted under 35 U.S.C. 154(b) by 174 days.

(21) Appl. No.: 12/990,159

(22) PCT Filed: Apr. 23, 2009

(86) PCT No.: PCT/US2009/041560
§ 371 (c)(1), (2), (4) Date: Oct. 28, 2010

(87) PCT Pub. No.: WO2009/134674
PCT Pub. Date: Nov. 5, 2009

(65) Prior Publication Data
US 2011/0046491 A1    Feb. 24, 2011

Related U.S. Application Data

(60) Provisional application No. 61/048,446, filed on Apr. 28, 2008.

(51) Int. Cl.
*A61B 6/00* (2006.01)
(52) U.S. Cl.
USPC .......................................... 600/473; 600/476
(58) Field of Classification Search
USPC .................................................. 600/473–480
See application file for complete search history.

(56) References Cited

U.S. PATENT DOCUMENTS

| | | | |
|---|---|---|---|
| 5,321,501 A | 6/1994 | Swanson et al. | |
| 5,361,316 A | 11/1994 | Tanaka et al. | |
| 5,842,995 A | 12/1998 | Mahadevan-Jansen et al. | |
| 6,445,939 B1 * | 9/2002 | Swanson et al. | 600/342 |
| 6,485,413 B1 * | 11/2002 | Boppart et al. | 600/160 |
| 7,091,500 B2 * | 8/2006 | Schnitzer | 250/458.1 |
| 7,295,311 B2 * | 11/2007 | Nicoli et al. | 356/344 |
| 7,428,052 B2 * | 9/2008 | Fujita | 356/479 |

(Continued)

FOREIGN PATENT DOCUMENTS

| | | |
|---|---|---|
| DE | 9308617 U1 | 7/1993 |
| WO | 2007048039 A1 | 4/2007 |

OTHER PUBLICATIONS

Hamamatsu Photonics K.K., "Multi-Fiber Adapter (MFA) for NIRO-200" brochure, Japan, 3 pages, 2005.

(Continued)

*Primary Examiner* — Sanjay Cattungal
(74) *Attorney, Agent, or Firm* — Lathrop & Gage LLP (57) ABSTRACT

An optode for a functional infrared diffuse optical neuroimaging system uses a GRIN lens and prism for coupling to an optical fiber at a right-angle to the lens. The lens is inserted into a grommet for attachment to an elastomeric cap worn by a subject. In an embodiment, the cap also has an array of electroencephalographic electrodes, with optodes arranged such that an optical path exists between a transmitter and a receiver optode beneath each electroencephalographic electrode. In an embodiment, quadfurcated optical cabling is used to permit illumination of each of multiple optodes with wavelengths provided from each of multiple lasers, and permitting each laser to illuminated multiple optodes.

9 Claims, 8 Drawing Sheets

(56) References Cited

U.S. PATENT DOCUMENTS

| | | | |
|---|---|---|---|
| 8,214,010 B2* | 7/2012 | Courtney et al. | 600/407 |
| 2004/0106856 A1 | 6/2004 | Kimura | |
| 2004/0260148 A1* | 12/2004 | Schnitzer | 600/108 |
| 2005/0143664 A1* | 6/2005 | Chen et al. | 600/478 |
| 2005/0251116 A1* | 11/2005 | Steinke et al. | 606/8 |
| 2006/0146338 A1* | 7/2006 | Fujita | 356/479 |
| 2007/0188855 A1* | 8/2007 | Shishkov et al. | 359/362 |
| 2008/0177138 A1* | 7/2008 | Courtney et al. | 600/109 |
| 2008/0177139 A1* | 7/2008 | Courtney et al. | 600/109 |
| 2008/0177183 A1* | 7/2008 | Courtney et al. | 600/463 |
| 2009/0018393 A1* | 1/2009 | Dick et al. | 600/109 |
| 2009/0043191 A1* | 2/2009 | Castella et al. | 600/425 |
| 2009/0054791 A1* | 2/2009 | Flusberg et al. | 600/478 |
| 2010/0069721 A1* | 3/2010 | Webler et al. | 600/182 |
| 2011/0137124 A1* | 6/2011 | Milner et al. | 600/160 |

OTHER PUBLICATIONS

Hamamatsu Photonics K.K., "NIRO-200 Near Infrared Oxgenation Monitor" brochure, Japan, 2 pages, 2003.

Schwarz, et al., "Ball Lens Coupled Fiber-Optic Probe for Depth-Resolved Spectroscopy of Epithelia Tissue," Optics Letters, vol. 30, No. 10, pp. 1159 1161, May 15, 2005.

Robinson, "GRIN Lenses Used in Microendoscope," Biophotonics International, pp. 60-61, Jul. 2004.

International Search Report and Written Opinion issued in related PCT Patent Application Serial No. PCT/US2009/041560, 19 pages, dated Oct. 21, 2009.

Invitation to Pay Fees issued in related PCT Patent Application Serial No. PCT/US2009/041560, 8 pages, dated Apr. 23, 2009.

* cited by examiner

10-20 EEG Electrode
Transmitter Optode
Receiver Optode

SYSTEM, OPTODE AND CAP FOR NEAR-INFRARED DIFFUSE-OPTICAL FUNCTION NEUROIMAGING

RELATED APPLICATIONS

The present application claims priority to U.S. Provisional Patent application No. 61/048,446, filed Apr. 28, 2008.

FIELD

The present application relates to an optode and an electrode-optode cap having multiple optodes for use in diffuse-optical imaging, and in particular in Near-InfraRed Diffuse-Optical Tomographic Functional NeuroImaging (NIR-DOTFNI) and correlation of NIR-DOTFNI with electroencephalography.

BACKGROUND

Functional Magnetic Resonance Imaging (fMRI) portrays particular parts of the brain that are active during specific activities of a subject. For example, experiments have illustrated those parts of the brain that are most active while performing mental arithmetic, or while opening and clenching a hand. Some differences have been noted between activity patterns of the mentally ill and those of "normal" subjects. fMRI operates by observing a coupled set of blood flow, volume and oxygenation changes in the brain, which are collectively termed the hemodynamic response. This hemodynamic response correlates with neuronal activity in the brain.

While the spatial resolution of fMRI is good, fMRI requires the subject's head remain stationary between poles of a magnet in a large, bulky, sometimes noisy, and usually expensive machine throughout a study. The requirement of stable head position renders fMRI impractical as a way to observe patterns of brain activity during many activities of a subject such as—for illustration and not by limitation—walking on a treadmill or, even holding an animated conversation. Further, the expense and immobility of fMRI machines precludes routine clinical use of fMRI on patients of average wealth in diagnosis and treatment monitoring of such psychiatric and neurological disorders as schizophrenia, Parkinsonism, epilepsy, multiple sclerosis, tumors, dementia, stroke rehabilitation and traumatic brain injury where it is expected that brain activity patterns may differ from the norm.

It is well known that light, including near-infrared light, penetrates to a limited extent through many human tissues, including the brain, skull and scalp; although that light is scattered by those tissues and some wavelengths are absorbed more than others. It is also well known that a pattern of absorbed wavelengths (or color) of light transmitted by tissue varies with oxygenation of blood in the tissue. Further, volume and flow of blood in the tissue is known to change scattering properties in the tissue.

Diffuse-optical functional neuroimaging is a technique of determining patterns of brain activity in mammalian or human subjects by projecting light into the subject into selected points on the subject's head while observing patterns of intensity, phase and color of scattered light emitted from the head at selected points. This may be performed using light having wavelengths in the near-infrared, with tomographic processing to obtain some three-dimensional localization of activity regions. It is expected that that brain activity patterns obtained through this near-infrared diffuse-optical functional neuroimaging (NIR-DOTFNI) can be correlated to activity patterns obtained through fMRI, and that these patterns may also correlate with brain activity patterns obtained through electroencephalography (EEG), magnetoencephalogram (MEG), transcranial Doppler sonography (TCD), positron emission tomography (PET), and single-photon emission computed tomography (SPECT).

NIR-DOTNFI is expected to provide a more portable apparatus for functional neuroimaging than possible with fMRI, thereby providing imaging useful for research, as well as diagnosing a variety of psychiatric conditions and identifying lesions including tumors in a subject. A second advantage of NIR-DOTFNI over fMRI is its superior temporal resolution over fMRI, which permits detailed quantitative analysis of the time-course of the hemodynamic response. A third advantage of NIR-DOTFNI over fMRI is its ability to determine changes in blood volume, oxygenation and flow through the use of multiple colors of laser light and spectroscopic analysis and computer modeling.

NIR-DOTNFI apparatus may also prove useful for determining truth and falsity of statements made by a suspect, although this is still a subject of research. Other potential applications of NIR-DOTNFI include, but are not limited to, brain computer interface (BCI), real-time neurofeedback for academic learning, real-time neurofeedback for rehabilitation training, acute patient monitoring in the neuro-intensive care unit, and attention monitoring for pilots and drivers.

An optode is a device for coupling light between optical or optoelectronic components (such as fiber bundles and/or lasers and/or photo-detectors) and a surface (such as skin or mucus membranes) of a subject. An optode may be used to couple light into the surface of the subject, out of the surface, or both. Optodes are typically connected to an end of a flexible light guide such as fiber-optic fibers or bundles or liquid light guides that in turn connect to light emitting devices such as lasers and/or light measuring and detecting apparatus such as photodiodes; some optodes may be used for light emission into the subject, some for light detection, and some for both. The optic fibers or bundles or liquid light guides may be bifurcated, quadfurcated, or further divided to or from the optode for the purpose of, for example, coupling multiple colors of laser light into the surface or coupling the light collected from multiple optodes into a single detector. The light emitting apparatus such as lasers and/or light measuring and detecting apparatus may be worn by the subject, or may be located several meters away.

Some optode designs have proved to be bulky, others have proved to be incompatible with EEG, MEG or fMRI, others have proved time consuming to attach to a subject, overly difficult to attach, or to be too painful to the subject for practical use.

U.S. Pat. No. 5,361,316 to Tanaka, et al., describes a probe for coupling light from an optical fiber into a body cavity for phototherapy, the probe having a ball lens. This device has no prism and does not lend itself to use as a compact optode for functional neuroimaging. A ball lens is also used in the coupling device of Schwarz, et al., Ball Lens Coupled Fiber-Optic Probe For Depth Resolved Spectroscopy Of Epithelial Tissue, Optics Letters, 15 May 2005 1159-1161. The coupling device of Schwarz lacks a prism, and has several stimulus fibers surrounding a central receive fiber in the same coupling device, and is intended to provide for infrared measurements of skin rather than deeper structures.

Hamamatsu's NIRO-200 system provides a multiple-channel device for generating infrared light, for coupling this light to an optode having a prism at the end of an optical fiber for coupling light into scalp regions without hair, and for receiving and measuring transmitted light. The prism optode design of Hamamatsu lacks any small optical component to displace the hair and make direct contact with scalp skin. This device also does not support simultaneous electroencephalography. The optodes of this device have no lens and is bulky enough to preclude the high-density optode arrays required for good resolution and accurate neuroimaging, and is bulky enough to preclude high density optode arrays combined with electroencephalographic arrays.

SUMMARY

An optode for a functional near-infrared diffuse optical neuroimaging system uses a GRIN lens and prism for coupling to an optical fiber at a right-angle to the lens. The lens is inserted into a grommet for attachment to an elastomeric cap worn by a subject. In an embodiment, the cap also has an array of electroencephalographic electrodes, with optodes arranged such that an optical path exists between a transmitter and a receiver optode beneath each electroencephalographic electrode.

DETAILED DESCRIPTION OF THE EMBODIMENTS

Figure 1:
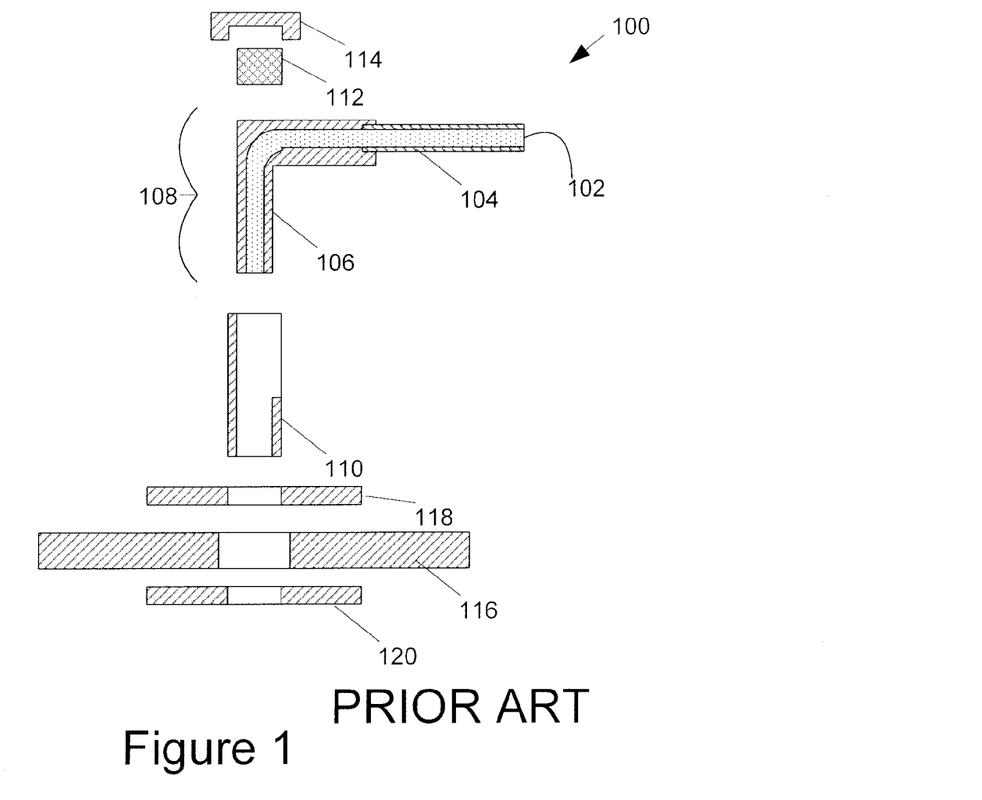
FIG. 1 is an exploded cross-sectional diagram illustrating a prior optode design.
Figure 2:
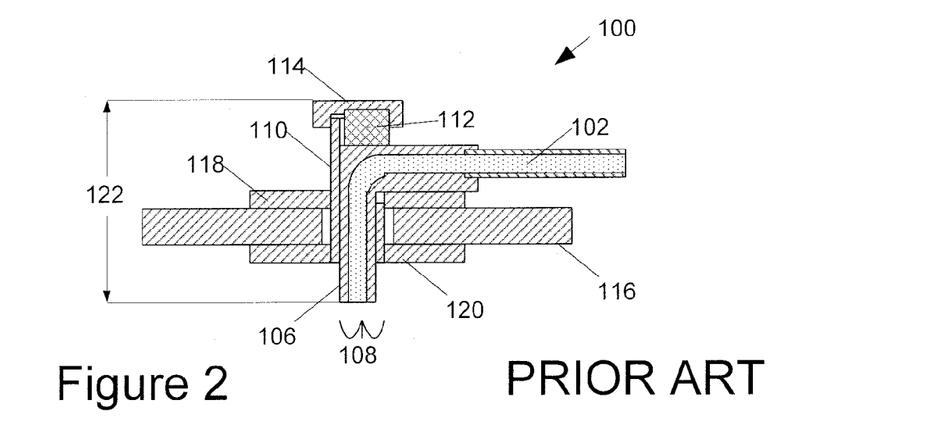
FIG. 2 is a cross-sectional diagram illustrating the prior art optode of FIG. 1 assembled.

In the prior art optode 100 embodiment of FIGS. 1 and 2, an optical fiber 102 or fiber bundle as known in the art of fiber optics and having a jacket 104 is secured within a 90-degree fitting 106 to form a cable termination assembly 108. Cable termination assembly 108 is slideably engaged within an optode body 110. An elastomeric spring 112 secured within the optode body 110 by an optode cap 114 tends to hold the cable termination assembly 108 in an extended position where it may contact a scalp of a mammal (not shown). Optode body 110 is secured into a polyethylene cap 116 by an upper washer 118 and a lower washer 120 or snap, which may be attached to the optode body 110 by glue, a friction fit, or by a shoulder (not shown) on the optode body 110.

Figure 3:
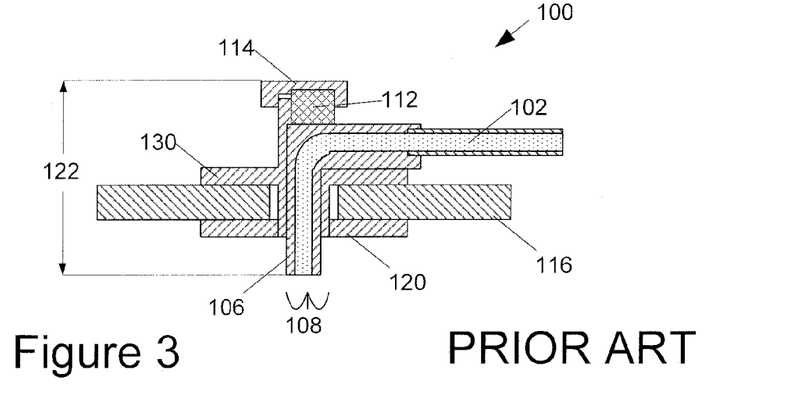
FIG. 3 is a cross-sectional diagram illustrating a prior art optode with a flange replacing the upper washer.

In an alternative prior embodiment, as illustrated in FIG. 3, upper washer 118 is replaced by a flange of optode body 130.

The prior art optode 100 has been found to be uncomfortable for subjects because of the sharp square bottom edge of the cable termination assembly 108 and because the elastomeric spring 112 does not always provide for adequate movement of cable termination assembly 108 in body 110. Further, the optode has an overall height 122 that is sufficient to interfere with performance of functional magnetic resonance neuroimaging while cap 116 is being worn by a subject.

Figure 4:
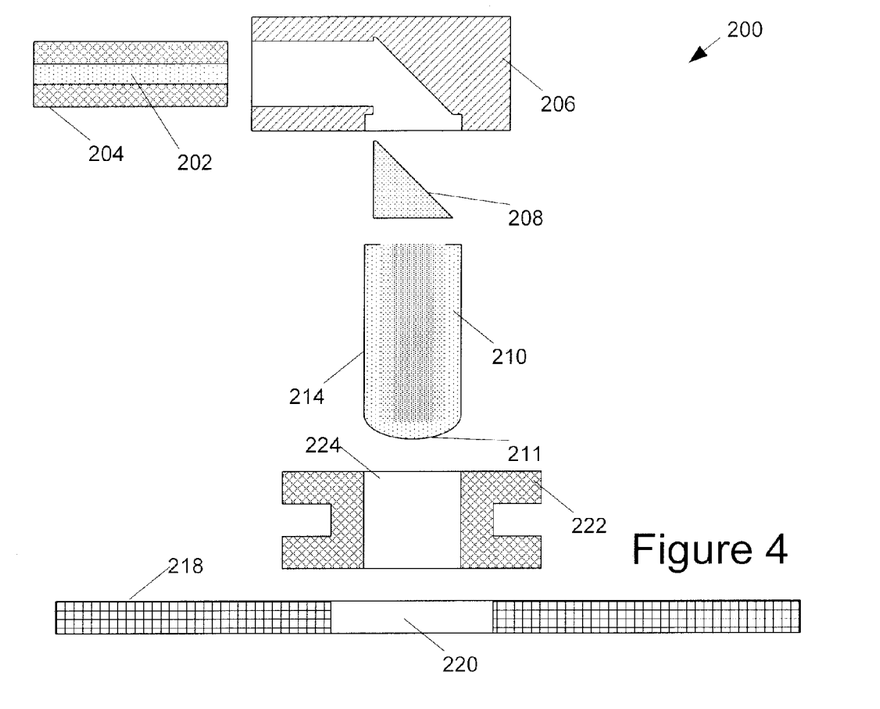
FIG. 4 is an exploded cross-sectional diagram illustrating a new optode design.
Figure 5:
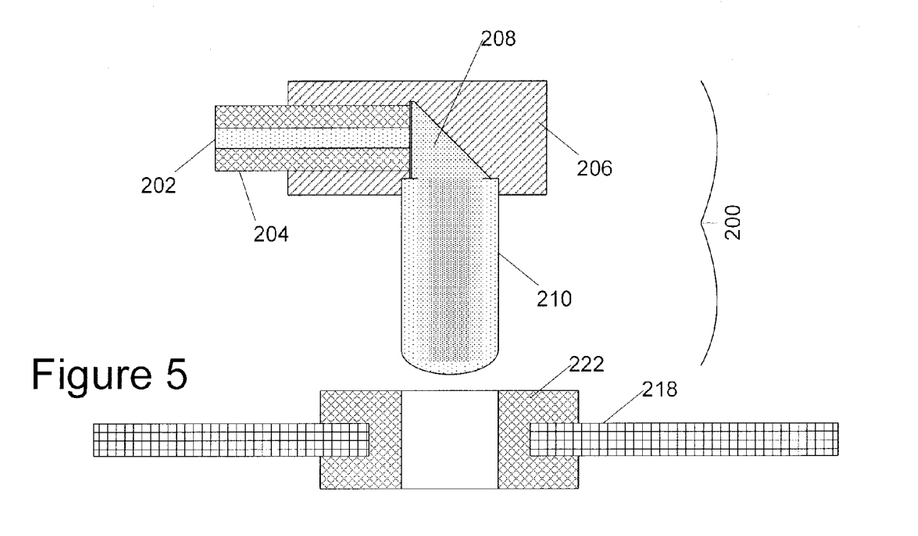
FIG. 5 is a cross-sectional diagram illustrating the optode of FIG. 3 partially assembled.
Figure 6:
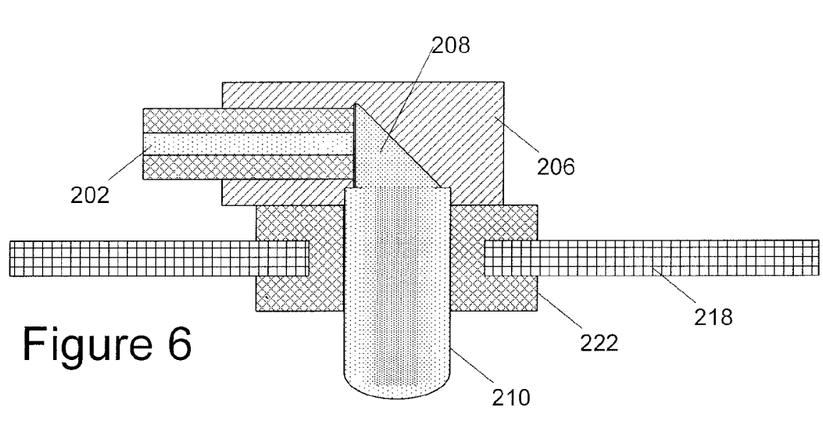
FIG. 6 is a cross-sectional diagram illustrating the optode of FIG. 3 fully assembled into an elastomeric cap.

The improved optode 200 of FIGS. 4, 5, and 6 has a fiber optic fiber or fiber bundle 202 as known in the art of fiber optics and as suitable for transmitting light of a desired wavelength. The optic fiber may have a jacket 204 and is inserted into and attached by glue or a collet into an optode body 206. Optical fiber 202 is optically coupled to a prism 208 also mounted within the optode body 206, and prism 208 is coupled to the high-density central portion of a flat end of a graded-index (GRIN) lens 210. GRIN lens has a convex curved end 211 for optical coupling to a scalp of a subject.

The GRIN lens 210 is also attached to the optode body 206, and has an outer circumferential surface 214.

An elastomeric cap 218, such as a cap formed from a sheet of neoprene rubber or woven elastic has holes 220. Elastomeric grommets 222, such as may be made from neoprene rubber, are inserted into cap 218. The elastomeric grommet 222 has a central hole 224 having diameter small enough to grip the circumferential surface 214 of the GRIN lens 210.

In use, GRIN lens 210 of each optode is inserted into hole 224 of the associated elastic grommet 222, as shown in FIG. 6; the cap is then secured to the head of a subject such that the convex surface or curved end 211 of each optode is held adjacent to the scalp of a subject (not shown), and the optical fiber 202 is coupled to an appropriate light source or light measurement device.

Figure 7:
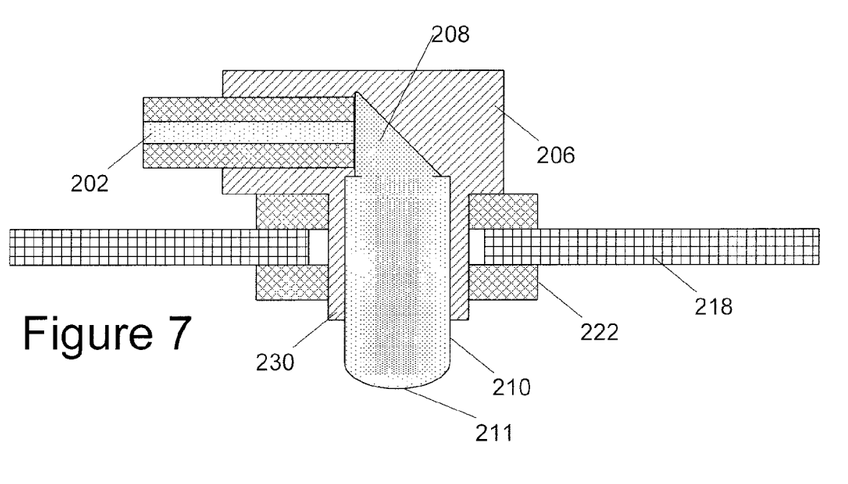
FIG. 7 is a cross sectional diagram illustrating an alternative embodiment of the optode.

An alternative embodiment of the optode is illustrated in FIG. 7. In this embodiment, the optode body 206 has a tubular extension 230 adjacent to a circumferential surface of GRIN lens 210 such that mechanical stresses are passed directly from body 206 extension 230 into grommet 222.

To perform functional neuroimaging, many optodes, typically in an array of from 24 to 64 optodes, are provided in a cap. Each optode is optically coupled to a suitable light source, such as a pulsed, continuous wave or frequency modulated laser, and/or a suitable light detection and measurement device such as an avalanche photodiode or a photomultiplier tube; the light sources periodically transmit light into the subject's head and the light detection and measurement devices periodically make measurements of transmitted light that are then processed by a computer to determine a pattern of blood oxygenation and volume in the brain of the subject.

Optodes typically operate in transmitter/receiver optode pairs. Transmitter optodes pass light from a light source through a scalp surface through tissue including bone into a subject's brain, some of this light is absorbed and some is scattered back out through bone and scalp back through a receiver optode to a light detection and measurement apparatus. Each transmitter optode, and each receiver optode, participates in multiple transmitter/receiver pairs. The detection and measurement apparatus detects variations in light absorption by tissue beneath and between the optodes of a pair. A computer processes these variations and measurements from multiple transmitter/receiver pairs into an image and may also perform spectroscopic analysis if multiple wavelengths of light are used.

It is known that heme changes color with oxygenation. Oxygenated arterial blood (having heme in hemoglobin) tends to be a brighter red while deoxygenated venous blood tends to have a bluer color. This is a consequence of changes in optical absorption of heme with oxygenation that occurs in the near-infrared as well as visible wavelengths.

It is therefore possible to determine both heme concentration and approximate oxygenation along the scattering path between transmitter and receiver optode pairs by measuring differences in scattering and absorption at several wavelengths of red and near-infrared light.

Each time a neuron fires, a small amount of that neuron's reserves of Adenosine TriPhosphate (ATP) is consumed in repolarizing the neuron; mitochondria of the neuron then recharge the ATP supply through a process that consumes oxygen. Areas of the brain having high activity therefore have higher oxygen consumption than those areas having low activity. This increased oxygen consumption in the active areas is associated with an increase in blood flow in those portions of the brain and results in localized increases in blood volume and oxygen levels—the so called hemodynamic response to brain activation that is monitored by fMRI. The increased blood flow may also lead to an increase in heme concentration along with changes in oxygen tension in active areas of the brain.

It is therefore desirable to measure differences in optical absorption along the paths between optodes at several wavelengths of light, as well as measuring overall absorption and phase changes in the emitted light; these measurements can give indications of heme concentration and oxygenation and flow and can thereby monitor changes in activity of areas of the brain along optical paths between optodes.

Each individual optode may, and usually does, participate in more than one transmitter/receive optode pair, with each pair having an optical path through the head between the optodes of the pair. Pairs may be distinguished by time multiplexing or by frequency encoding modulation on the lasers. Pairs and pathways may also be distinguished by operating transmitter optodes at different wavelengths while using frequency-selective light detection and measurement devices. Pairs, including transmit optodes of the same groups, operating at the same time and frequency but positioned sufficiently far apart on the head that the light transmission along paths between them is effectively zero can also be distinguished from each other and attenuation of pathways between such pairs may be measured simultaneously.

Figure 8:
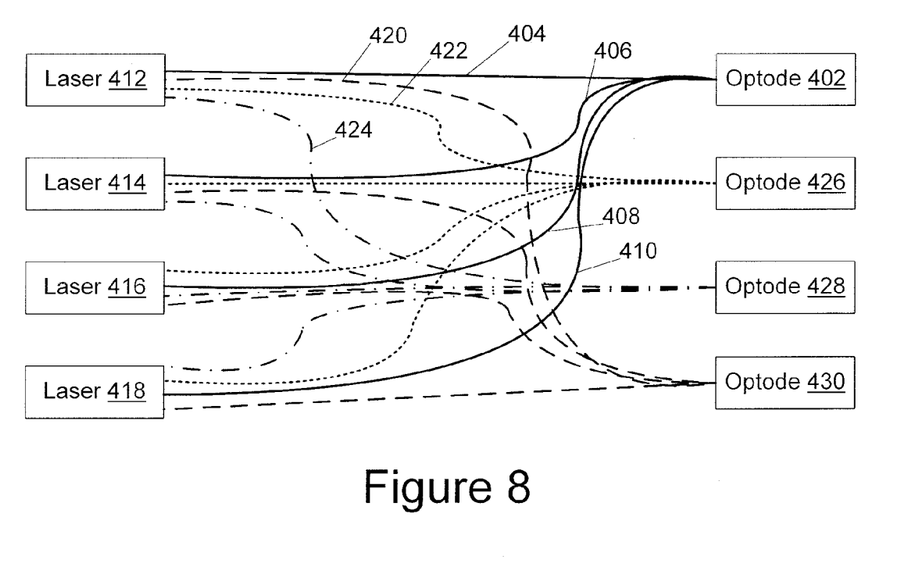
FIG. 8 is an illustration of quadfurcated fibers permitting illumination of the optodes with multiple wavelengths using one laser per optode.

In an embodiment, transmit optodes are grouped into transmit optode groups, as illustrated in FIG. 8. In a transmit optode group each transmit optode, such as optode 402 is fed by an optical guide that is an optical fiber bundle that is quadfurcated—or divided into four separate subguides or strands 404, 406, 408, 410, where each strand 404, 406, 408, 410 has at least one optical fiber, the optical fiber of each strand extending into the optode body 206 and coupled to prism 208.

In this embodiment, each strand 404, 406, 408, 410 is coupled to be fed by a separate laser of a laser group, such as laser 412 feeding into strand 404, laser 414 feeding into strand 406, laser 416 feeding into strand 408, and laser 418 feeding into strand 410. Each of the four lasers 412, 414, 416, 418 of a laser group operates at a separate wavelength, in an embodiment laser 412 is at six hundred ninety nanometers, laser 414 operates at seven hundred eighty five nanometers, laser 416 operates at eight hundred eight nanometers, and laser 418 operates at eight hundred thirty nanometers.

Since it would be expensive, albeit functional, to have a four laser laser-group, including lasers 412, 414, 416, 418, for each transmit optode; in an embodiment each laser, such as laser 412, feeds strands, such as strands 404, 420, 422, 424 coupled to multiple optodes, such as optodes 402, 426, 428, 430. This architecture permits construction of the system for significantly lower cost than fMRI machines. Similarly, the remaining lasers 414, 416, and 418 of the laser group are coupled through optical fiber strands of quadfurcated cables to all four optodes 402, 426, 428, 430, of the optode group.

Figure 12:
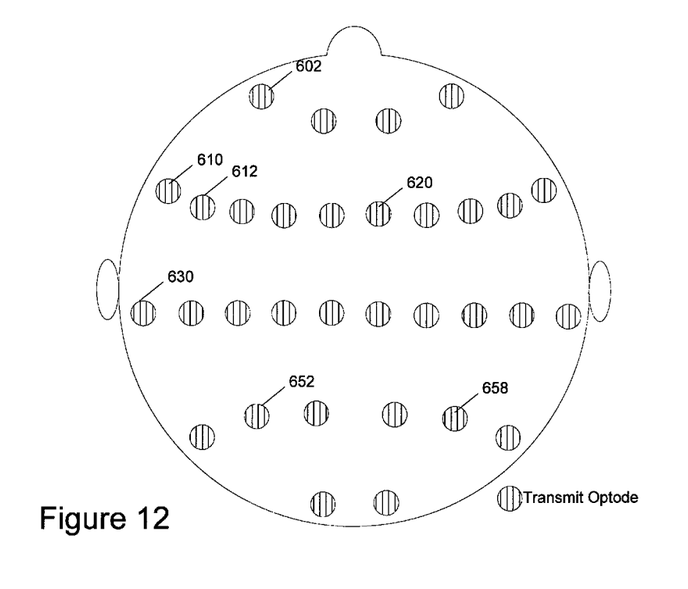
FIG. 12 is an illustration of optode placement in the cap for use with quadfurcated fiber allowing individual lasers to illuminate multiple widely-separated optodes.

The four optodes of each transmit optode group are placed in the cap at locations such that pathways through the head to each associated receive optode are short enough to produce strong signals from only one transmit optode of each group, while pathways from other optodes of the group are significantly longer. For example, as illustrated in FIG. 12, if optode 610 is in a first group, nearby transmit optodes 602, 612, 630 belong to different groups that have transmit lasers either illuminated at different times, or carrying different frequency modulations. The remaining optodes in the first group are well separated on the head and in the cap, for example and not limitation the optodes of the first group may include optodes 620, 652, and 658 in addition to optode 610. This permits disambiguation of the optode-optode paths.

In a time-division embodiment, one laser selected from lasers 412, 414, 416, 418 of the transmit optode group is illuminated at a time, and that illumination time is distinguished by being illuminated at a time separated from times of illumination of similar wavelengths of other transmit optode groups.

In an alternative embodiment, each laser of lasers 412, 414, 416, 418 is amplitude-modulated at a frequency that is unique within the group, but all four lasers 412, 414, 416, 418 generate light simultaneously. With this embodiment, electronics associated with each receive optode determines at least an intensity of modulation at each laser modulation frequency to disambiguate the lasers and to determine spectral characteristics of absorption along paths from transmit optodes to the receive optode.

Since all four optodes 402, 426, 428, and 430, of the optode group are illuminated simultaneously, at the same wavelength, and with the same modulation, these optodes are preferably placed well apart on the head such that light emitted from each optode, such as optode 402, does not reach receive optodes near, and having significant optical paths to, another optode, such as optode 426 of the group.

In an alternative embodiment, the fibers of each transmit optode are bifurcated instead of quadfurcated, and each is coupled to only two lasers operating on different wavelengths.

A standard arrangement of electroencephalographic electrodes, known as the 10-20 electrode pattern, is illustrated in FIG. 7. The 10-20 international system includes 19 scalp electrodes and 2 reference electrodes on the ears.

Figure 11:
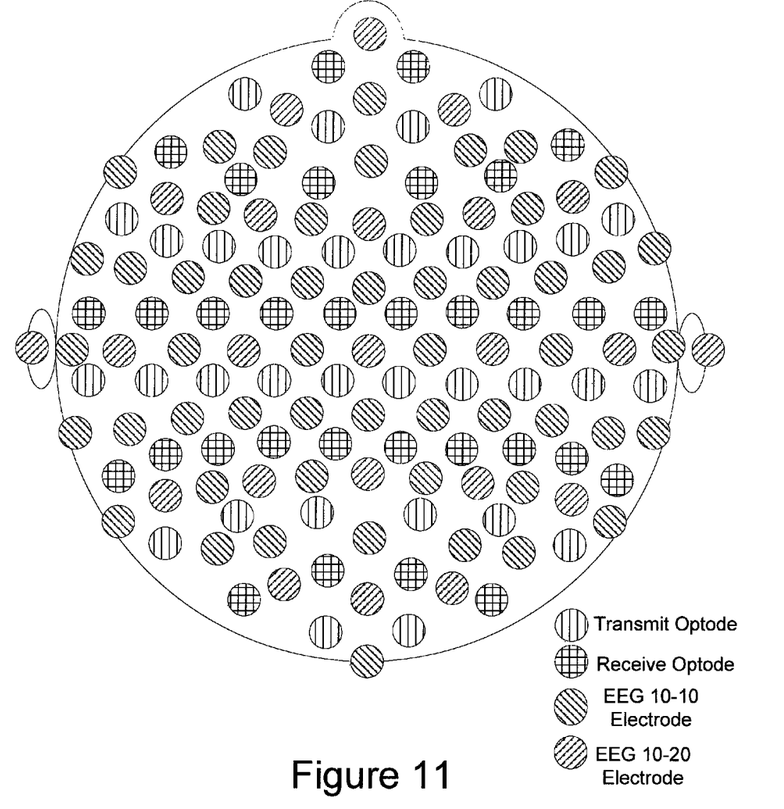
FIG. 11 is an illustration of a 75-electrode, 64-optode, optical neuroimaging and electroencephalographic combination cap pattern.

In an embodiment where it is desired to correlate electroencephalographic measurements with NIR-DOTFNI, the cap has an array of low-contact-area electroencephalographic electrodes interspersed with a pattern of transmitter and receiver optodes for NIR-DOTFNI. For example, in the embodiment of FIG. 11, the electroencephalographic electrodes are laid out in a cap in a standard 10-10 electrode pattern, which includes the 10-20 electrodes. In the embodiment of FIG. 11, most of the electroencephalographic electrodes (see FIG. 11 for key), with exception of reference electrodes and some electrodes near periphery of the pattern, are arranged such that a transmitter and a receiver optode of a sixty-four optode array are on approximately opposite sides of each of the electroencephalographic electrodes; such that the optode array provides for measurement of neurovascular activity beneath at least three fourth of the electroencephalographic electrodes.

Figure 10:
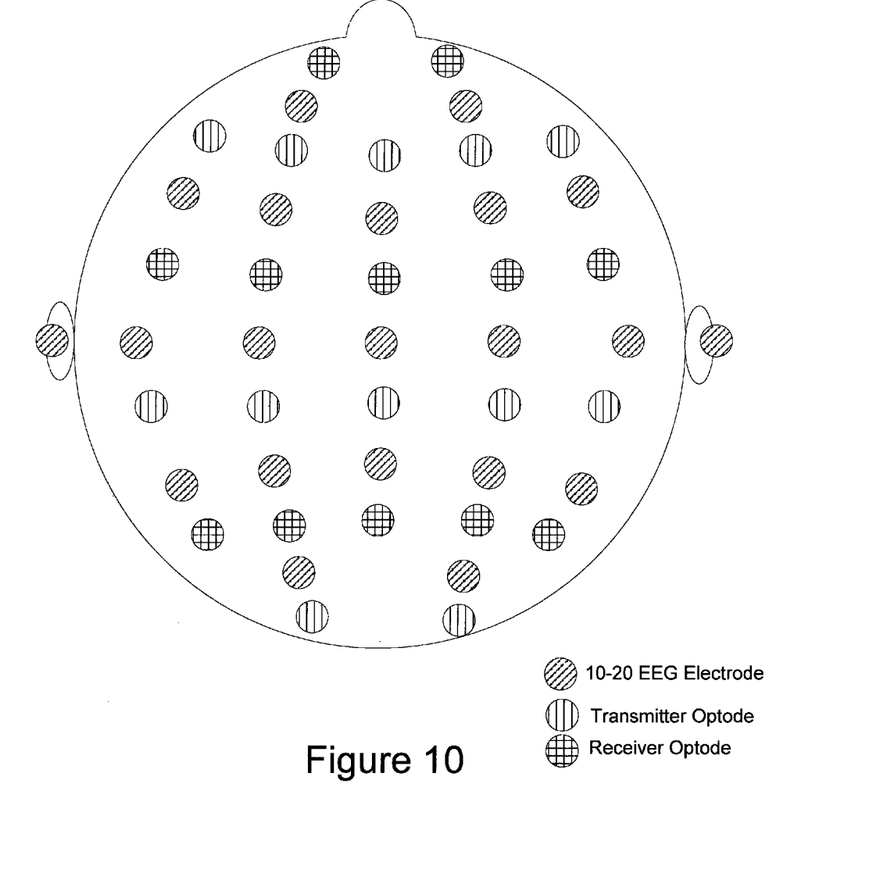
FIG. 10 is an illustration of a 21-electrode, 24-optode, optical neuroimaging and electroencephalographic pattern.

The cap of FIG. 10 using the optodes of FIG. 4 may be used without shaving a subject's hair because the GRIN lenses tend to displace hair and to make contact primarily with skin of the scalp.

Figure 9:
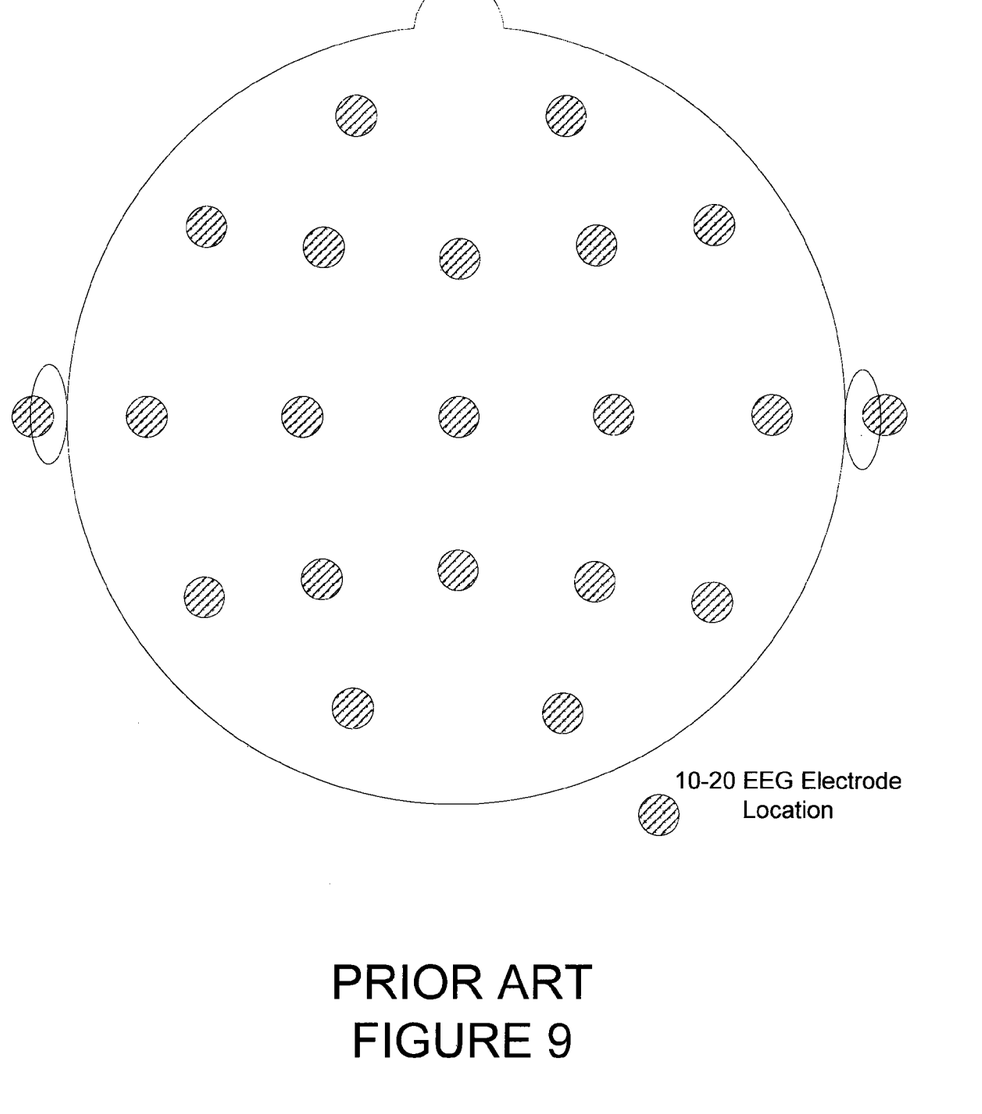
FIG. 9 is an illustration of a 21-electrode prior-art 10-20 electroencephalographic pattern.

Similarly, the embodiment of FIG. 10 provides an arrangement for the cap where each electroencephalographic electrode in the standard "10-20" pattern of FIG. 9, with exception of reference electrodes, has a transmitter and a receiver optode of an optode array are on approximately opposite sides of each of the electroencephalographic electrodes; such that the optode array provides for measurement of neurovascular activity beneath at least three fourths of the electroencephalographic electrodes.

In the embodiments of FIGS. 10 and 11, the electroencephalographic electrodes are sensitive to neural activity primarily beneath each electrode, while the optodes are primarily sensitive to activity along an optical path describing an arc between the optodes, the arrangements of FIGS. 10 and 11 therefore provide coincident electroencephalographic and NIR-DOTFNI imaging.

An embodiment according to FIG. 11 has quadfurcated transmit optode groups as illustrated in FIG. 12.

Figure 13:
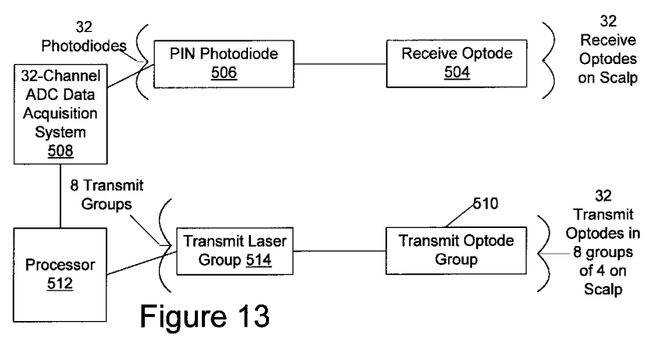
FIG. 13 is an illustration of a system for functional neuroimaging using the cap of FIG. 11 and the optodes of FIG. 4.

The transmit optodes of each group are coupled to transmit lasers as illustrated in the system diagram of FIG. 13. In this embodiment, each of the thirty-two receive optodes 504 is coupled by a straight-through optical fiber—a fiber that is neither bifurcated nor quadfurcated—to an avalanche photodiode 506 for detecting transmitted light from one or more transmit optodes. In a more-expensive alternative embodiment, each receive optode 504 is coupled by a bifurcated or quadfurcated optical fibers, these fibers couple through filters for selecting specific laser wavelengths to avalanche photodiodes.

The avalanche photodiode 506 is coupled to a data acquisition system that uses signals from the photodiode 506 to measure at least an attenuation at each wavelength from transmit optodes 510 of at least one transmit optode group; this attenuation information is provided to a processor 512 for image construction. The processor 512 also activates transmit lasers 514 of each transmit optode group, providing near-infrared light to the transmit optodes.

It should be noted that the matter contained in the above description or shown in the accompanying drawings should be interpreted as illustrative and not in a limiting sense. The following claims are intended to cover generic and specific features described herein, as well as all statements of the scope of the present method and system, which, as a matter of language, might be said to fall therebetween.

What is claimed is:

1. An optode for interfacing light to biological tissue comprising:
    at least one flexible light guide;
    a prism optically coupled to the flexible light guide;
    a graded incidence (GRIN) refractive lens having a circumferential surface, a convex surface and a flat surface, the flat surface optically coupled to the prism; and
    a body for holding the optical fiber, prism, and GRIN lens, the body configured to maintain the fiber, prism, and GRIN lens in fixed relationship having a right angle between an axis of the fiber and an axis of the GRIN lens;
    wherein the convex surface of the graded incidence refractive lens is capable of interfacing light to biological tissue.

2. The optode of claim 1 further comprising an elastomeric grommet having a hole, the circumferential surface of the GRIN lens secured in the hole of the elastomeric grommet, the grommet and body retaining the optode in a hole of an optode-positioning device.

3. The optode of claim 1 wherein the body has a tubular extension, the extension having an inner surface in contact with the circumferential surface of the GRIN lens and an outer surface in contact with an elastomeric grommet, the grommet and body retaining the optode in a hole of an optode-positioning device.

4. The optode of claim 1 wherein the GRIN lens and flexible light guide are optimized for transparency in the infrared.

5. The optode of claim 1 wherein the flexible light guide comprises at least one optical fiber.

6. The optode of claim 1 wherein the flexible light guide comprises at least two optical fibers, and wherein the flexible light guide is at least bifurcated into a first and a second subguide.

7. An optode for interfacing light to biological tissue comprising:
    at least one flexible light guide;
    a prism optically coupled to the flexible light guide;
    a GRIN lens having at least a convex surface and a second surface, the second surface optically coupled to the prism; and
    a body for holding the flexible light guide, prism, and GRIN lens, the body configured to maintain the guide, prism, and GRIN lens in fixed alignment having right angle between an axis of the fiber and an axis of the GRIN lens;
    wherein the convex surface of the lens is capable of interfacing light to biological tissue; and
    wherein the flexible light guide comprises a plurality of optical fibers and divides into a plurality of subguides, and wherein at least a first optical fiber of the plurality of fibers extends from the prism to an end of a first subguide of the subguides, and wherein at least a second optical fiber of the plurality of fibers extends from the prism to an end of a second subguide of the subguides.

8. The optode of claim 7 wherein the body has a tubular extension, the extension having an inner surface in contact with a circumferential surface of the lens and an outer surface for contacting an elastomeric grommet.

9. The optode of claim 7 wherein the GRIN lens and flexible light guide are optimized for transparency in the infrared.

* * * * *